United States Patent [19]

Pelenc et al.

[11] Patent Number: 5,773,256
[45] Date of Patent: Jun. 30, 1998

[54] METHODS FOR THE PRODUCTION OF ESTERS OF α-GLUCOSIDES AND USES THEREOF

[75] Inventors: Vincent P. Pelenc; Francois M.B. Paul, both of Toulouse; Pierre F. Monsan, Mondonville, all of France

[73] Assignee: Ulice SA, Riom, France

[21] Appl. No.: 462,669

[22] Filed: Jun. 5, 1995

Related U.S. Application Data

[62] Division of Ser. No. 193,139, May 25, 1994.

[30] Foreign Application Priority Data

Aug. 12, 1991 [FR] France ................................ 91/10244

[51] Int. Cl.[6] .......................... C12P 19/44; C12P 19/18; C12P 7/64; C07H 13/06
[52] U.S. Cl. ................................ 435/74; 435/97; 435/99; 435/105; 435/134; 435/135; 536/4.1; 536/102; 536/115; 536/124
[58] Field of Search .................... 435/74, 97, 99, 435/105, 135, 134; 536/115, 124, 102, 4.1

[56] References Cited

U.S. PATENT DOCUMENTS

| | | | |
|---|---|---|---|
| 4,683,297 | 7/1987 | Yanami et al. | 536/18.6 |
| 5,191,071 | 3/1993 | Kirk et al. | 536/4.1 |
| 5,200,328 | 4/1993 | Kirk et al. | 435/101 |

FOREIGN PATENT DOCUMENTS

| | | |
|---|---|---|
| 0102558 | 3/1984 | European Pat. Off. . |
| 0219673 | 4/1987 | European Pat. Off. . |
| 0334498 | 9/1989 | European Pat. Off. . |
| 0377831 | 7/1990 | European Pat. Off. . |
| 2125582 | 9/1972 | France . |
| 2542318 | 9/1984 | France . |
| 3718340A1 | 12/1988 | Germany . |
| 63-287496 | 11/1988 | Japan . |
| 2214914 | 9/1989 | United Kingdom . |
| 8901480 | 2/1989 | WIPO . |
| 9009451 | 8/1990 | WIPO . |

OTHER PUBLICATIONS

Yalpani, Studies in Organic Chemistry 36, Chapter 9, pp. 371–405, Elsevier, New York, 1988.
ATCC Catalogue of Fungi/Yeasts, 17th Ed., 1987, p. 45.
Fogarty, W.M. and Benson, C.P. (1982) "Measurement of Glucose Transfer to Glycerol by *Aspergillus Niger* Transglucosidas", Biotechnology Letters, 4:61–64.
Itano, K. et al. (1980) "Stereospecific Preparation of Monoglucosides of Optically Active *trans* –1, 2–Cyclohexandiols by Enzymic Trans–D–Glucosylation, and [13]C–N.M.R. Spectroscopy of the Resulting Mono–D–Glucopyranosides", Carbohydrate Research 87:27–34.
Pan, S.C. (1970) "Synthesis of Estriol 16β–(β–D–Glusides) by Enzymic Transglucosylation", Biochemistry 9:1833–1838.
Bjorkling, Fredrik et al. (1989) "A Highly Selective Enzyme–catalyzed Esterification of Simple Glucosides", J. Chem. Soc., Chem. Commun.: 934–635.
Adelhorst, Kim et al. (1990) "Enzyme Catalysed Preparation of 6–O–Acylglucopyrano–sides", Synthesis: 112–115.

*Primary Examiner*—Leon B. Lankford, Jr.
*Assistant Examiner*—Francisco C. Prats
*Attorney, Agent, or Firm*—John P. White; Cooper & Dunham

[57] ABSTRACT

Disclosed is a process of enzymatically preparing α-glucoside esters. First, α-glucosides are produced by placing an acyclic alcohol or a mixture of acyclic alcohols having a water solubility of at least 2.7% v/v at 20° C. in contact with starch, maltodextrins or maltose, in the presence of a purified enzymatic preparation having α-transglucosylation activity, wherein the enzymatic preparation is free of β-glucosidase activity. Then, the α-glucosides are contacted with at least one fatty acid and a preparation having lipase activity to produce the α-glucoside esters, which may then be recovered. The preparation having α-transglucosylation activity may originate from a fungus such as *Talaromyces duponti, Aspergillus niger, Aspergillus oryzae* or *Aspergillus batatae*.

27 Claims, 6 Drawing Sheets

METHODS FOR THE PRODUCTION OF ESTERS OF α-GLUCOSIDES AND USES THEREOF

This is a division of application Ser. No. 08/193,139, filed May 25, 1994.

The present invention relates to a process for the stereospecific enzymatic manufacture of α-glucosides from starting materials which are inexpensive and available in large quantities, especially starch and the maltodextrins, as well as directly from agricultural starting materials which may contain them, such as flours or semolinas. The invention also concerns a process for the esterification of the α-glucosides thus obtained.

Starch is very widely distributed in nature. In fact, it constitutes a major plant food source, and large quantities are placed in reserve by plant organisms in order to maintain the life of the stem or the tuber during the winter dormancy, and to ensure that the embryo develops in the course of the germination.

Taking into account the abundance of this substance, numerous attempts at industrial exploitation have been made, most of them involving a hydrolysis reaction. Starch is hydrolyzed by dilute acids, with complete acid hydrolysis giving D-glucose. Fragments of higher molecular weight, the dextrins, are obtained by controlled acid hydrolysis and by the action of temperature. Starch may also be hydrolyzed by enzymes (amylases).

The hydrolysis products of starch may be used in the manufacture of glucosides. These compounds, in particular the alkylglucosides, are used as biodegradable surfactants and nonionic detergents. They may be used as emulsifying agents in pharmaceutical, cosmetic and food products.

The chemical synthesis of the alkyl glucosides from glucose has already been described (for example, EP-A-0, 301,298). This type of chemical process may, however, comprise a very high number of different steps and always give an anomeric mixture of α/β-alkylmono- and alkylpolyglucosides. These mixtures, which possess no precise physico-chemical characteristics, have all the disadvantages associated therewith and, especially, the absence of a precise melting point, the absence of regioselectivity and the possibility of secondary reactions.

The enzymatic manufacture of alkylglucosides from maltose has also been proposed (S. C. Pan, Biochemistry, vol. 9, No. 8, 1970, pp 1833–1838 and Itano K. et al, Carbohydrate Research, 87, 1990, 27–34). Pan describes the transglucosylation of an alcohol such as butanol with, as glucose donor, maltose in the presence of an *Aspergillus niger* culture supernatent. The identity of the enzyme(s) contained in the supernatent and responsible for the transglucosylation has not been investigated. The anomeric configuration (α or β) of the alkylglucosides obtained has not been verified. Itano describes the enzymatic production of cyclohexanediol α-glucoside using, as glucose donor, maltose and, as glucose acceptor, trans-1,2-cyclohexanediol. This reaction uses a crude mixture of various enzymes used in the agro-food industry, most of which are hydrolases. These preparations additionally contain unidentified enzymes.

The yields obtained according to these enzymatic processes are low and do not permit synthesis of the alkylglucosides on an industrial scale. Moreover, the anomeric configuration of the products obtained is sometimes unpredictable on account of the numerous enzymes present during the reaction and, especially, on account of an unidentified β-glucosidase activity.

Finally, Fogarty et al (Biotechnology Letters, vol. 4, 1, 61–64, 1982) describes the production of α-glycerolglucoside by the enzymatic transglucosylation of glycerol with, as glucose donor, α-methylglucoside. The enzyme used in this reaction is purified transglucosidase from *A. niger*. Under the conditions described, the glycerol can only act as a glucose acceptor with a very limited number of substrates. These results show that transglucosidase, like many transferases, is capable of acting on a relatively high number of acceptors, but, on the other hand, the number of substrates or donors which it may use is very limited.

The subject of the present invention is to provide a method for the stereospecific manufacture of α-glucosides giving rise to high yields which are suitable for an exploitation on an industrial scale and which make it possible to use, as starting materials, starch or maltodextrins, as well as agricultural starting materials of high starch content such as flours or semolinas. The method sought must be simple, direct and inexpensive. Another subject of the invention is to provide a process for the treatment of crude starchy material such as starch or maltodextrins, which make it possible to produce compounds of high added value, comprising, for example, α-glucoside esters.

The inventors have now surprisingly observed that α-glucosides may be synthesized on an industrial scale by enzymatic α-transglucosylation, using starch or maltodextrins as substrates or "glucose donors" and alcohols as co-substrates or "glucose acceptors".

It is totally unexpected that polymeric molecules such as starch or α-maltodextrins can act as glucose donors in this reaction. As indicated above, α-transglucosidase may carry out the transfer of a glucosyl residue onto a relatively high number of acceptors (alcohol in the present case), but can only use very few molecules as substrates.

The invention more particularly relates to a process for the enzymatic manufacture of α-glucosides (also known under the name α-glucopyranosides), characterized by placing at least one alcohol, whose only functional group(s) is(are) hydroxyl group(s), in contact with starch, maltodextrins or maltose, in the presence of a purified enzymatic preparation having an α-transglucosylation activity.

The products obtained by this process are α-glucosides consisting of at least one molecule of glucose and of an alcohol, whose carbon chain is of variable length and structure according to the type of alcohol which has participated in the reaction. The product is devoid of β-glucoside. The biosynthesis is carried out under mild reaction conditions, at average temperature (20° C. to 70° C., for example between 30° C. and 60° C.) and at pH between 3 and 7, preferably 4 and 6. The formation of glucose degradation products is thus avoided.

In the context of the invention, an enzymatic preparation "having an α-transglucosylation activity" is understood to refer to any enzymatic preparation capable of carrying out the transfer of a glucose molecule (from starting materials consisting of starch or containing starch, or consisting of starch hydrolysates or containing starch hydrolysates) onto the alcohol.

Purified should be understood to mean that the enzymatic preparation is deprived of any enzymatic activity capable, under the conditions used, of catalyzing the manufacture of substances other than α-glucosides, that the enzymatic preparation is such that it avoids the formation of secondary products, that the enzymatic preparation is especially devoid of β-glucosidase activity.

The enzymatic preparation may consist of a single enzyme having an α-transglucosylation activity.

The enzymatic preparation may also consist of several enzymes such that either each one of them has an α-transglucosylation activity, or their combined enzymatic activities are such that they confer an α-transglucosylation activity on the above-mentioned enzymatic preparation.

It may be an "authentic" α-transglucosidase, also known as "α-transglucosylase", that is to say an enzyme of the transferase type. This type of enzyme is normally recognized by its capacity to synthesize oligosaccharides in dilute medium (for example 100 g/L maltose).

α-Transglucosidases which may be mentioned are fungal α-transglucosidases such as those from *Aspergillus niger, A. batatae. A. oryzae* or *Talaromyces duponti*. The α-transglucosidases from *Aspergillus niger* and *Talaromyces duponti* are particularly preferred. It is advantageous to use these enzymes in purified form, the preparation thus being devoid of any β-glucosidase activity. The presence of β-glucosidase in the enzymatic preparation effectively prevents the stereospecific synthesis of the α-glucosides.

α-Transglucosidase from *Aspergillus niger*, available under the commercial name of TRANSGLUCOSIDASE-L (Amano Pharmaceutical Corporation Ltd, Japan), is normally devoid of β-glucosidase and may be used in the process of the invention without additional purification. On the other hand, that derived from *Talaromyces duponti* (also known under the name of 1,4-α-D-glucan-6-α-D-glycosyltransferase) is advantageously subjected to an additional purification step, by ion exchange, in order to remove the β-glucosidase, but has the advantage of a great thermostability. This enzyme is described in the European Patent Application EP-A-0,219,673.

It is also possible to use a mixture of purified enzymes, for example α-transglucosidases from various types of fungi, on condition that other enzymes are not present and that the various enzymes function under the same conditions.

The enzyme having an α-transglucosylation activity may also be a purified hydrolase which possesses, as "marginal" property, the capacity to carry out α-transglucosylation reactions. This type of enzyme may generally be recognized by its capacity to form glucose in dilute medium (for example 100 g/L maltose). Examples of this type of enzyme which may be mentioned are the hydrolases such as α-glucosidase.

Although these enzymes are capable of carrying out types of reactions other than α-transglucosylation, the reaction medium, composed exclusively of starch, maltodextrins or maltose, and alcohol, favor the formation of α-glucosides.

It is possible to use, as substrates or "glucose donors", according to the invention, starch, maltodextrins or maltose or a mixture of these substances, as well as agricultural starting materials which may contain these substances.

When maltose is used as substrate, it may be present in the form of a mixture with other substances originating from starchy materials, for example, when the substrate is a partial hydrolysate of starch, maltose may be present with maltodextrins. Maltose may also be used alone. The yields of α-glucoside obtained from maltose are sometimes poorer than those obtained from other types of substrate, and are, for example, of the order of 10 to 15% (calculated as in Example 1 below).

Maltodextrins constitute a particularly preferred substrate or "glucose donor" according to the process of the invention. They are partial hydrolysates of starch, consisting of a mixture of oligosaccharides of variable molar mass and displaying (1-4)-α linkages between the glucose units. The maltodextrins may derive from a partial acid hydrolysis of starch or a thermal or enzymatic treatment of starch. This type of product is also available on the market and, on account of its purity, is particularly preferred when the α-glucosides obtained are intended to be used in the pharmaceutical industry.

According to another variant of the process of the invention, the substrate, or "glucose donor", may also be soluble starch. This product, which may be assimilated to maltodextrins, consists of starch which has been rendered soluble by an acid prehydrolysis, for example according to the Lintner process.

According to another particularly preferred embodiment of the invention, the substrate consists of native starch. Sources of native starch which may be mentioned are cereals, tubers and leguminous plants, as well as any other plant. Among the preferred cereals there may be mentioned wheat, maize, barley, oats, rice, rye, triticale (a hybrid of rye and wheat), buckwheat and sorghum. The preferred tubers are potatoes and manioc. Peas and beans are a source of leguminous starch. The cereals may be used in the form of whole grains, grain fractions (resulting, for example, from an enzymatic, chemical, thermal or mechanical treatment of the grain), or any other product arising from the grinding of grain, such as flour or semolina.

When the substrate is native starch, the action of the enzyme which is capable of carrying out the α-transglucosylation is associated with the action of a hydrolase, in order to render the starch accessible to the α-transglucosylation. The hydrolase liberates maltodextrins and maltose from the native starch into the medium. These substrates are then used as glucose donors by α-transglucosidase which glucosylates the alcohols present in the medium. The hydrolase is preferably used simultaneously with α-transglucosidase.

As hydrolases, it is preferable to use endo-amylases, for example α-amylase (E.C.: 3.2.1.1), originating, for example, from fungi or from *Bacillus licheniformis*. Endo-amylases have the advantage of carrying out "endo" cleavages in the starch molecule, without liberating molecules of low molecular weight (that is to say glucose). In fact, α-transglucosidases are not capable of using glucose as a substrate. The production of glucose by amylase would thus prevent the subsequent manufacture of α-glucosides. As for maltose, although it may serve as a substrate for α-glucosidase, the alkylglucoside yield thus obtained is lower than with maltodextrins or starch. The ratio between the transferable glucose and the unused glucose is higher in the case of a maltodextrin than in the case of maltose.

Simultaneous use of amylase and α-transglucosidase is preferred, competition for the soluble molecules being established between the two enzymes. The simultaneous progress of the two enzymatic processes leads in this way to an improvement in the yield.

The effectiveness of amylase on starch varies according to the botanical origin of the starch and according to the nature of the amylase.

The relative concentrations of the substrate, the enzyme and the alcohol are for the substrate, approximately 10 g/l to approximately 800 g/l and in particular approximately 100 g/l to approximately 400 g/l for the alcohols, from approximately 10 g/l to approximately 800 g/l, and in particular from approximately 50 g/l to approximately 400 g/l for the enzyme, from approximately 5 U/ml to approximately 1,000 U/ml, and in particular from approximately 50 U/ml to approximately 200 U/ml.

The glucose acceptor according to the invention is an alcohol of simple functionality, that is to say an alcohol which carries no functional groups other than the hydroxyl groups. A mixture of various alcohols may be used. All the alcohols capable of acting as glucose acceptors in the reaction, and which do not inhibit the enzyme activity, may be used.

The preferred alcohols are alkanols, ethylenic alcohols, acetylenic alcohols, cyclic alcohols or phenols. Acyclic alcohols are particularly preferred, especially saturated alkanols having, for example, between 2 and 24 carbon atoms, and saturated polyols. According to the process of the invention, the alcohol may be a monohydric alcohol, or may also be a polyol, for example a diol or a triol. Diols are particularly preferred, such as propanediols and butanediols. Primary, secondary and tertiary alcohols may be used in the reaction of the invention, the primary and secondary alcohols being particularly advantageous.

It may be a water-miscible or at least partially water-miscible alcohol. In this case, the alcohol advantageously has a solubility of at least 2.7% v/v at 20° C. In most cases, these alcohols contain between 1 and 6, and often between 1 and 5, carbon atoms.

Examples of preferred soluble alcohols which may be mentioned are: isopropanol, n-butanol, isobutanol, isopentanol, propanol, pentanediol, hexanediol, 1-buten-3-ol, 1-butyn-3-ol, cyclohexanol, etc., or a mixture of at least two of these alcohols. The reaction is conducted in aqueous medium, the alcohol often being used at the limit of its solubility.

When the alcohol is partially soluble in water, it is possible to carry out the process of the invention in a two-phase medium, that is to say an aqueous phase in which the alcohol(s) is (are) dissolved at a concentration lower than the limit of their solubility, and an organic phase in equilibrium with the aqueous phase and composed of the saturated buffer alcohol. The use of a two-phase medium exerts a favorable effect on the yield of α-glucosides. This system is particularly advantageous when the α-glucoside obtained by the α-transglucosylation reaction may, above a certain concentration, constitute a substrate for the enzyme. For example, α-butylglucoside may act as a substrate for α-transglucosidase. In this case, the reaction proceeds in the aqueous phase, and the α-glucoside is extracted from the aqueous phase into the organic phase, preventing destruction of the glucoside by the enzyme.

The use of an ethylenic alcohol such as 1-buten-3-ol leads to the presence of an unsaturated bond in the glucoside. This permits the subsequent use of the glucoside in polymerization reactions or the preparation of chiral synthons (intermediate molecules) for pharmaceutical or chemical use.

According to a particularly advantageous embodiment, the soluble alcohol is a monohydric alkanol having from 1 to 5 carbon atoms. These alcohols give rise to α-alkylglucosides in which the alkyl chain has from 1 to 5 carbon atoms.

It is also possible to use water-insoluble alcohols, for example, alkanols having more than six carbon atoms, in particular between 12 and 18 carbon atoms, or else fatty alcohols (primary aliphatic alcohols) such as dodecyl alcohol, tetradecyl alcohol, hexadecyl alcohol, octadecyl alcohol, decyl alcohol, undecyl alcohol and tridecyl alcohol, and the like. Steroids may also be mentioned as water-insoluble alcohols. The use of fatty alcohols is advantageously accompanied by the use of short alcohols (1 to 6 carbon atoms), which are partially water-soluble and which act as solvents for the fatty alcohols and as glucose acceptor.

Hydrophobic alcohols, such as those mentioned above, may participate in the enzymatic α-transglucosylation reaction by using a two-phase system (that is to say water and an organic solvent). The hydrophobic alcohol is thus dissolved in a solvent such as nitrobenzene, whereas the substrate and the enzyme are dissolved in an aqueous solution. The two solutions are subsequently mixed and stirred. The α-transglucosylation takes place at the interface. It is also possible to use other organic solvents, for example acetone, on condition that the enzyme activity is not affected.

On account of the surfactant properties of the α-alkyl glucosides, whose alkyl chain has between 12 and 18 carbon atoms, the use, as alcohol, of fatty alcohols is particularly preferred.

The α-glucoside yields obtained by the process of the invention vary according to the glucose donor and according to the extraction method. With, for example, maltodextrin or starch as substrate and a two-phase organic solvent system for extraction of the product, the yields may reach 20 to 30%. Maltose gives yields of 10 to 15%. The yields are calculated in the following way:

$$\frac{\alpha\text{-glucoside produced, moles}}{\alpha\text{-glucoside produced + glucose produced, moles}} \times 100$$

The products obtained by the process of the invention are stereospecific (α) and are normally monoglucosides. It is possible, for example, by adding an α-alkylglucoside as "additional" substrate to the reaction medium, to bring about the formation of diglucosides, that is to say maltosides. These maltosides have very similar properties to those of the glucosides.

The stereospecificity of the product may be verified by carrying out the hydrolysis of a sample with an enzyme which can only act on the α-anomers, for example α-glucosidase. Maltase is an example of an α-glucosidase which is suitable for this verification.

On account of the absence of β-anomer in the product of the invention, certain physical characteristics, such as the melting point and the solubility of the glucoside, are very narrowly defined. This precision is advantageous for a use in the pharmaceutical, cosmetic and chemical industry in general.

In addition, the enzyme used during the α-transglucosylation is in the purified state. The product of the invention is thus devoid of contaminants arising from secondary enzymatic reactions. The need to carry out numerous purification steps for the products of the reaction is thus removed.

The invention also relates to the α-glucosides, in particular the α-alkylglucosides as obtained by the process of the invention. These products are thus characterized by the absence of contaminants normally associated with glucosides produced by the chemical route or by the enzymatic route using enzyme mixtures. α-Butylglucoside is a particularly preferred product of the invention. More particularly, the α-glucosides of the invention are free of β-anomers and of any contaminant arising from secondary enzymatic reactions.

Extraction of the product from the reaction medium is thus all the more simple since, apart from the product, it only contains the excess alcohol, the remaining glucose donor and the glucose produced in the course of the reaction. The extraction may be done in a suitable organic solvent, chosen in accordance with the solubility of the product. According to a preferred embodiment, extraction of the α-glucoside, for example α-butylglucoside, is carried out in continuous fashion by means of a liquid column of extraction solvent, for example butanol. According to this variant, the reaction medium is to begin with passed through a first column containing the immobile transglucosidase, and then onto the liquid extraction column. The alcoholysis reaction and the extraction of the product then occur in continuous fashion. α-Butylglucoside is recovered in the form of a syrup after evaporation of the butanol, and the butanol is recycled for use as a substrate. By using this type of two-phase extraction, the yields of products reach 35 to 40%.

The glucosides produced according to the invention have a multitude of applications.

Alkylglucosides, in particular those in which the alkyl chain has up to 6 carbon atoms, for example α-butylglucoside, may be used as liquid detergent additives, as emulsion additives for modifying the viscosity without bringing about phase-separation, or as co-surfactant in microemulsions. In fact, the presence of hydrophobic and hydrophilic groups in these molecules enables them to be used in emulsions, for example cosmetic and pharmaceutical creams, for modifying the properties of an emulsion, without destabilizing it. Since the glucosides of the invention are manufactured by a biosynthesis from natural materials, they are particularly suited to cosmetic and pharmaceutical applications of this type.

The alkylglucosides, and in particular α-butylglucoside, may also be used as additives in the plastics, rubber and PVC industries for example, as softeners in melamine resins. The use of α-butylglucoside prevents the resin from having an excessively brittle nature. They may also be used as additives in industrial and domestic cleaning compositions or in maintenance products.

Alkylglucosides in which the alkyl chain has at least 8 carbon atoms are used as biodegradable nonionic surfactants and detergents, displaying foaming, lubricating, emulsifying and moisturizing properties.

Since they are stereospecific and are obtained by an enzymatic synthesis process from plant materials, the products of the invention are particularly suitable for pharmaceutical, cosmetic or food use, for example as nontoxic and non-irritant emulsifying agents.

The glucosides of the invention also constitute an excellent starting material in the manufacture of polyether polyols, for example, of rigid foams based on polyurethane. The products thus obtained have an improved thermostability and excellent physical properties. The glucosides, in particular the alkylglucosides, may also be used as polyols in the manufacture of alkyd and polyester resins or as a chemical intermediate for the synthesis of monomers which may be used in polymerization reactions.

The alkylglucosides of the invention having short alkyl chains ($C_1$ to $C_6$) may serve as starting materials in the manufacture of surface-active agents, for example by replacing the alkyl chain by an alkyl chain having at least 8, and preferably at least 12, carbon atoms. These alkylglucosides of long alkyl chain have excellent emulsifying and foaming properties and are biodegradable.

Another type of surface-active agent may be produced by the esterification, preferably in the positions $C_2$ and $C_6$, of lower alkylglucosides of the invention. The emulsifiers thus obtained have moisturizing properties and are also biodegradable.

According to a particularly preferred variant of the invention, esterification of the α-glucosides is carried out via the enzymatic route by placing the α-glucoside in contact with a fatty acid or with a mixture of different fatty acids and an enzymatic preparation having lipase activity. This type of reaction has been described by Björkling et al (J. Chem. Soc., Chem. Comm., 1989, p 934–935). Combining this enzymatic esterification reaction with the alcoholysis reaction of the invention makes it possible to manufacture pure α-glucoside esters from starch, maltodextrose or maltose. The esterification may be carried out after the alcoholysis reaction or simultaneously with the alcoholysis.

According to this variant of the invention, the α-glucoside is preferably an alkylglucoside having between 1 and 5 carbon atoms or a mixture of these α-alkylglucosides. α-Butylglucoside is particularly preferred. The fatty acid advantageously contains between 8 and 20 carbon atoms. Caprylic ($C_8$), capric ($C_{10}$), lauric ($C_{12}$) and palmitic ($C_{16}$) acids are particularly preferred. It is also possible to use a mixture of several fatty acids.

The esterification is catalyzed according to this embodiment by an enzymatic preparation having lipase activity, for example, a lipase originating from *Mucor miehei* (for example Lipozyme®), *Candida antartica, Humicola sp., Candida cylindracea* and *Pseudomonas sp.* Any lipase may be used which is capable of carrying out the reaction on the chosen fatty acid. It may be a purified preparation containing a single enzyme or, alternatively, a mixture of several enzymes showing lipase activity. The enzyme having lipase activity may be immobilized on a solid support.

The esterification reaction is carried out at a temperature situated approximately between room temperature and 80° C., on condition that it is a temperature at which the fatty acid is in liquid form, and at which the enzyme is stable. The absence of solvent represents a considerable advantage from the economic and environmental points of view.

The products obtained by the enzymatic esterification, without solvent, of the α-glucosides of the invention are mono- and diester mixtures. The operating conditions may be optimized in order to make it possible to obtain approximately 80% of monoesters. The reaction is regiospecific, the esterification taking place to begin with in the position $C_6$, and subsequently in the position $C_2$, $C_3$ or $C_4$ depending on the enzyme. The diester may be a mixture of 2,6-, 3,6- and 4,6-diesters. In this case, the product comprises the monoester and a mixture of diesters. The diester is preferably a 2,6-diester. The production of a proportion of diesters is inevitable since, above a certain monoester concentration the enzyme recognizes the monoester as substrate rather than α-glucoside. When only a single fatty acid is used in the esterification, the diester carries two identical groups. On the other hand, if a mixture of two fatty acids are used, the diester is a mixed diester, for example butyl 2-O-lauryl-6-O-stearyl-α-D-glucopyranoside. The choice of fatty acids makes it possible to vary the properties of the esters produced, in particular the H.L.B (hydrophilic/lipophilic balance).

The product of the esterification may be extracted from the reaction medium by a suitable organic solvent, such as diethyl ether or, on the industrial scale, hexane. Any solvent in which the α-glucoside and the fatty acid are insoluble, may be used. Recovery of the esters is also possible without addition of organic solvent. The product may be used as it is without purification, after removal of the immobilized enzyme.

The α-glucoside esters thus produced are free from β-anomers and from secondary reaction products normally associated with esters obtained from less pure glucosides or via a chemical route. These esters have a multitude of industrial applications and may be used for any standard application for esters of this type. The α-glucoside esters and, in particular, the α-alkylglucoside esters are nonionic, non-irritant, non-toxic and biodegradable surfactants which have properties such as foaming, emulsifying, solubilizing, moisturizing, dispersing, wetting or lubricating properties. They are advantageously used as additives in cosmetic and pharmaceutical and agro-food products, or alternatively in chemistry or in the detergent industry as surfactants or whitening agent precursors. In agriculture, they may be used as inert adjuvants for augmenting the effectiveness of plant protection products, especially herbicides, fungicides and insecticides, and for the treatment of cultures and agricultural products in general.

The figures show various aspects of the invention, especially:

a) reaction time: 10 min
b) reaction time: 23 hours
c) α,β-butylglucoside mixture.

Figure 3A:
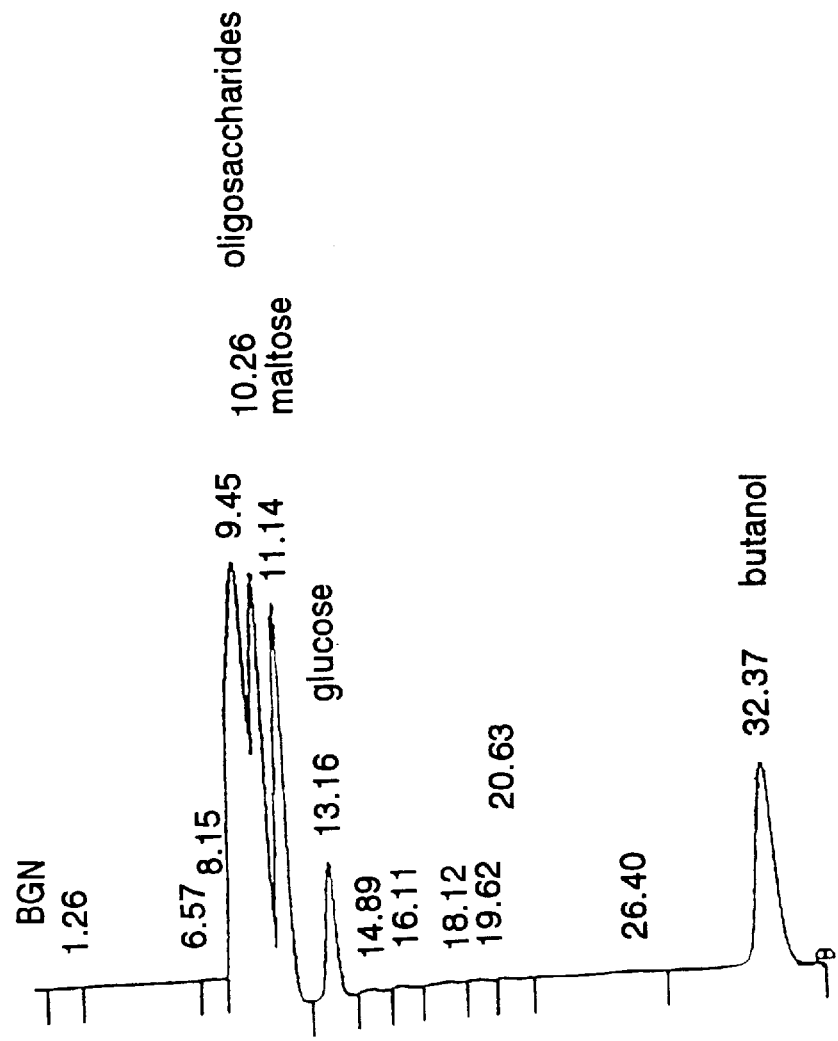
Figure 3B:
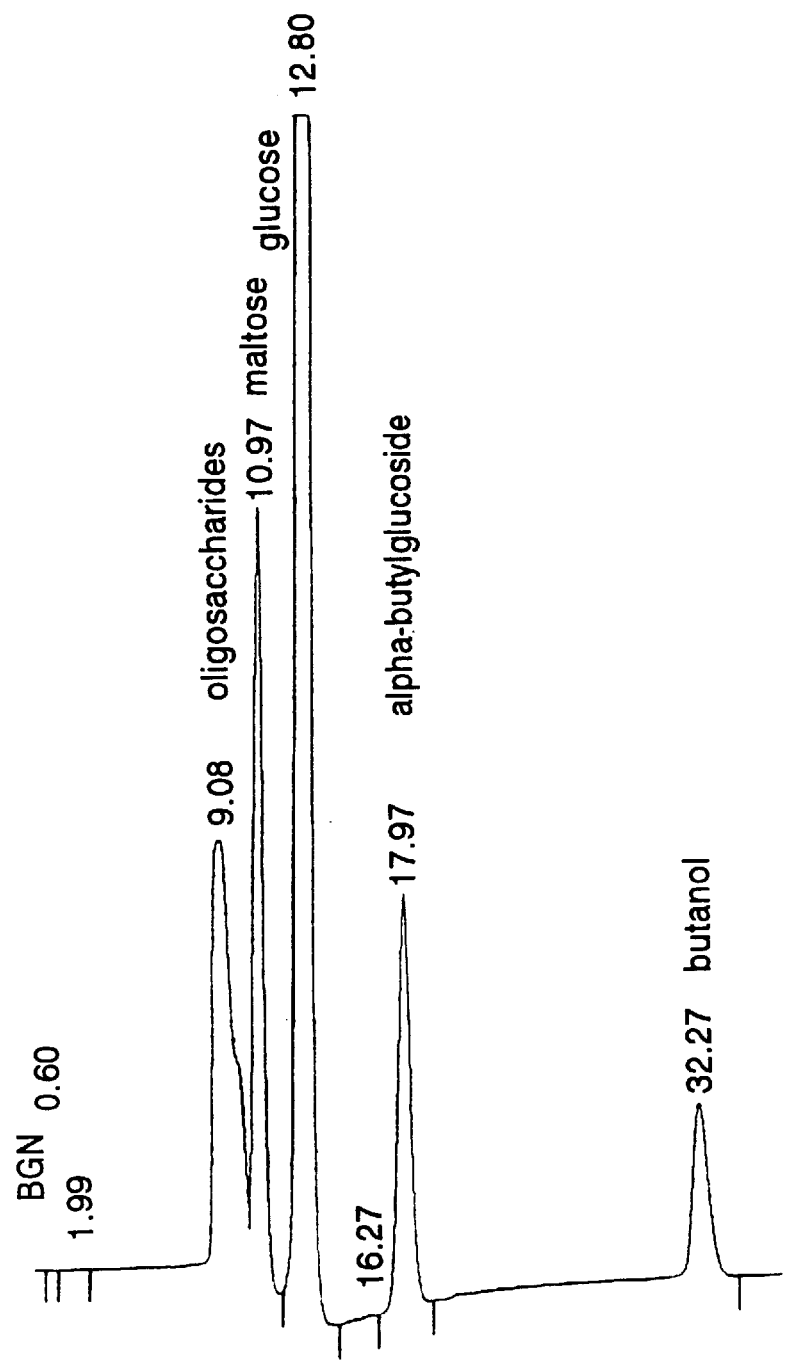

FIG. 3 illustrates HPLC chromatograms of the medium for the synthesis of α-butylglucoside with transglucosidase from *Aspergillus niger* from insoluble starch: two-phase liquid medium:

a) reaction time: 10 min
b) reaction time: 7 hours.

EXAMPLES

Example 1

Production of α-butylglucoside from soluble starchy substrates in the presence of butanol with the aid of α-transglucosidase from *Talaromyces duponti* a) Assay of the α-transglucosidase activity

Assay of the α-transglucosidase activity is carried out at 60° C. in the following medium:

maltose: 100 g/l
sodium acetate buffer pH 4.5: 50 mM
α-transglucosidase: 1 U/ml

The medium is analyzed after reaction for 15 and 24 hours by an HPLC technique (DIONEX Carbopack column, conductimetric detection) which allows the separation and the detection of the panose formed in the course of the reaction.

1 unit of α-transglucosidase (U) is the quantity of enzyme which catalyzes the production of 1 micromole of panose (6-O-α-D-glucopyranosylmaltose) per hour under the conditions presented above.

b) Production of α-butylglucoside

The production of α-butylglucoside is carried out in the aqueous medium of the following composition:

Butanol: 9% (v/v)
Sodium acetate buffer pH 4.5: 50 mM
α-transglucosidase from *Talaromyces duponti*: 100 U/ml
Substrate: 100 g/l This medium is incubated at the temperature of 50° C. for 70 hours. Samples are withdrawn, diluted (1/10) in water, heated to 90° C. to stop the reaction, and then analyzed by high performance liquid chromatography (HPLC) on a column of ion-exchange resin in calcium form. The eluent is ultrapure water.

Under these analysis conditions the α-butylglucoside is separated from the β-butylglucoside and the mono- and oligosaccharides. From the area of the corresponding peak it is possible to calculate the α-butylglycoside concentration in the reaction medium and the glucose transfer yield defined in the following way:

$$\frac{\alpha\text{-butylglucoside, mM}}{(\alpha\text{-butylglucoside + glucose), mM}}$$

The results are presented in Table 1:

TABLE 1

α-butylglucoside produced from soluble substrates and transfer yields after reaction for 70 hours.

| Substrate | α-Butylglucoside in mM | Yield in % |
|---|---|---|
| Maltose | 21 | 10 |
| Maltopentaose | 50 | 15 |
| Maltodextrins | 48 | 19 |
| Soluble starch | 40 | 15 |

Figure 1:
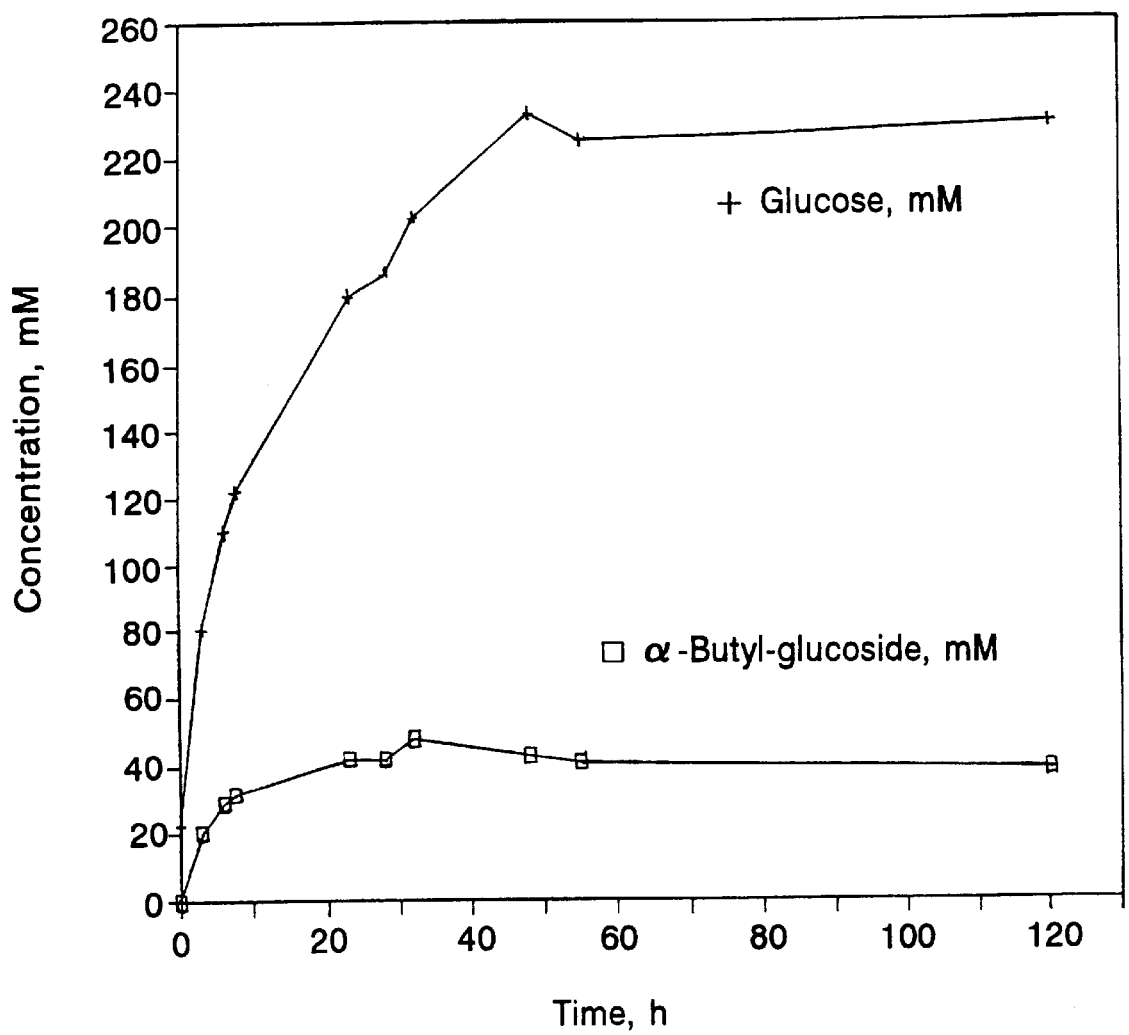
FIG. 1 shows the production of glucose and of α-butylglucoside from maltodextrins with the aid of α-transglucosidase from *Talaromyces duponti*.

The production of α-butylglucoside and glucose was followed in the course of the reaction. The change in the concentration of these two products is indicated in FIG. 1.

The production of α-butylglucoside takes place with the four starchy substrates tested in this example. With maltodextrins, the α-butylglucoside concentration is greater than 10 g/l.

Example 2

Production of α-butylglucoside from insoluble starch in the presence of butanol with the aid of α-transglucosidase from *Talaromyces duponti*.

The reaction medium is constituted as in Example 1. The substrate here is insoluble starch. α-Amylase from *Bacillus licheniformis* (5 U/ml) is added to the medium in order to make it possible to use the insoluble substrates.

The samples withdrawn from the reaction medium are treated as in Example 1, but are centrifuged and filtered before the HPLC injection.

The results are presented in Table 2:

TABLE 2

α-butylglucoside produced from insoluble starch and transfer yields after reaction for 70 hours.

| Substrate | α-Butylglucoside in mM | Yield in % |
|---|---|---|
| Insoluble starch + α-amylase | 28 | 16 |

The insoluble starch may also be used as a substrate of the reaction.

Example 3

Production of α-butylglucoside from insoluble starchy substrates in a liquid two-phase medium with the aid of α-transglucosidase from *Talaromyces duponti*.

The reaction medium consists of two liquid phases of the following composition:

Aqueous phase (volume: 0.5 ml):
Butanol: 9% (v/v)
Sodium acetate buffer pH 4.5: 50 mM
α-transglucosidase from *Talaromyces duponti*: 100 U/ml
α-amylase: 5 to 500 U/ml
Substrate: 100 g/L Organic phase (volume: 0.5 or 2 ml)

Butanol saturated with 50 mM sodium acetate buffer, pH 4.5.

The reaction media are vigorously stirred before each withdrawal and then treated as in Example 2.

Several media were investigated, with two reaction volumes and two α-amylase preparations. The influence of the α-amylase content of the medium was also studied.

The HPLC analysis results for the reaction media are presented in Tables 3 and 4:

TABLE 3

α-butylglucoside produced and transfer yields after reaction for 70 hours in a liquid two-phase medium (α-amylase from *Bacillus licheniformis*, 5 U/ml)

| Substrate Reaction volume ml | α-Butylglucoside mM | Yield % |
|---|---|---|
| Insoluble starch 1 | 46 | 23 |
| Insoluble starch 2.5 | 25 | 23 |

TABLE 4

α-butylglucoside produced and transfer yields from cornflour with the aid of α-transglucosidase from *Talaroiuyces duponti* in a liquid two-phase medium (reaction volume: 1 ml)

| Source and activity of the α-amylase | α-Butylglucoside mM | Yield % |
|---|---|---|
| B. licheniformis 5 U/ml | 14 | 24 |
| B. licheniformis 50 U/ml | 15 | 19 |
| B. licheniformis 500 U/ml | 9 | 14 |
| A. niger 5 U/ml | 10 | 14 |
| A. niger 50 U/ml | 12 | 17 |
| A. niger 500 U/ml | 9 | 19 |

The use of crude cereal flour is entirely possible for the synthesis of α-butylglucoside with the aid of α-transglucosidase from *Talaromyces duponti*.

The use of a liquid two-phase medium makes it possible to improve the production of α-butylglucoside. In Table 3, it is seen that 46 μmoles of α-butylglucoside were synthesized in the 1 ml volume medium, whereas 62.5 μmoles were synthesized in the 2.5 ml medium from the same amount of substrate and of enzymes.

Example 4

Production of α-alkylglucosides from soluble starchy substrates with the aid of α-transglucosidase from *Talaromyces duponti* in the presence of a mixture of alcohols.

Three media were constituted in the following way:

Maltodextrins: 100 g/l

α-Transglucosidase from *Talaromyces duponti*: 100 U/ml

Sodium acetate buffer pH 4.5: 50 mM

The three media contain a mixture of mono-alcohols:

| | Test 1 | Test 2 | Test 3 |
|---|---|---|---|
| Butanol | 9% | 45% | — |
| Pentanol | — | — | 25% |
| Isopropanol | — | 25% | 45% |
| Water | 91% | 30% | 30% |

The media were incubated at 50° C. for 120 hours and then analyzed according to the method described in Example 1. The analysis results are indicated in Table 5:

TABLE 5

Alkylglucosides produced in the presence of alcohol mixtures (reaction volume: 1 ml)

| | Test 1 | Test 2 | Test 3 |
|---|---|---|---|
| α-butylglycoside g/L | 10 | 5 | — |
| Isopropylglucoside g/L | — | 2 | 6 |
| Pentylglucoside g/L | — | — | 2 |

Example 5

Production of α-butylglucoside from insoluble starch with the aid of α-transglucosidase from *Aspergillus niger*

Two media were prepared and then incubated according to the procedure indicated in Example 3.

One-phase aqueous medium (volume: 20 ml)

Butanol: 9% (v/v)

Sodium acetate buffer pH 5.5: 50 mM

α-Transglucosidase from *Aspergillus niger*: 100 U/ml

α-amylase from *Bacillus licheniformis*: 5 U/ml

Insoluble starch: 100 g/l

Two-phase liquid medium (volume: 40 ml)

Aqueous phase (volume: 20 ml):

Butanol: 9%

Sodium acetate buffer pH 5.5: 50 mM

α-Transglucosidase from *Aspergillus niger*: 100 U/ml

α-amylase from *Bacillus licheniformis*: 5 U/ml

Insoluble starch: 100 g/l

Organic phase (volume: 20 ml):

Butanol saturated with 50 mM sodium acetate buffer, pH 5.5

Figure 2A:
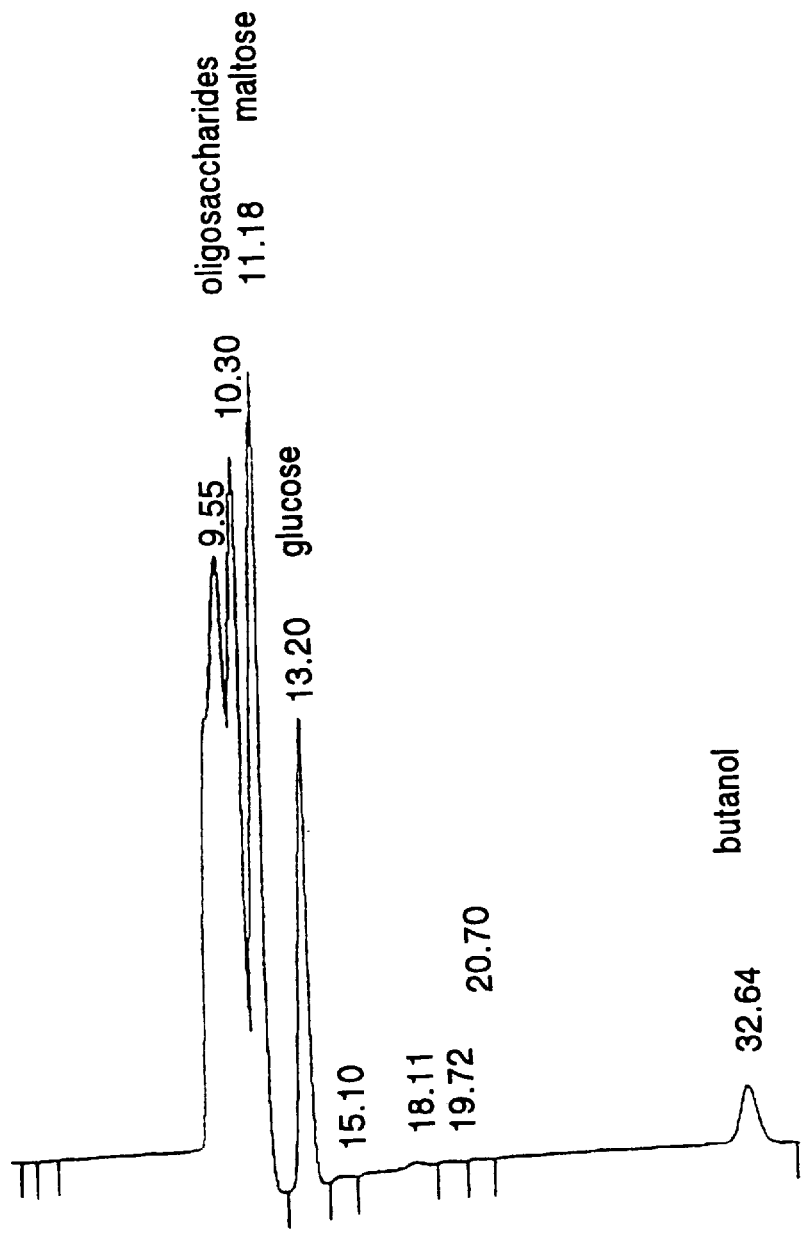
FIG. 2 illustrates HPLC chromatograms of the medium for the synthesis of α-butylglucoside with transglucosidase from *Aspergillus niger* from insoluble starch: one-phase liquid medium.
Figure 2B:
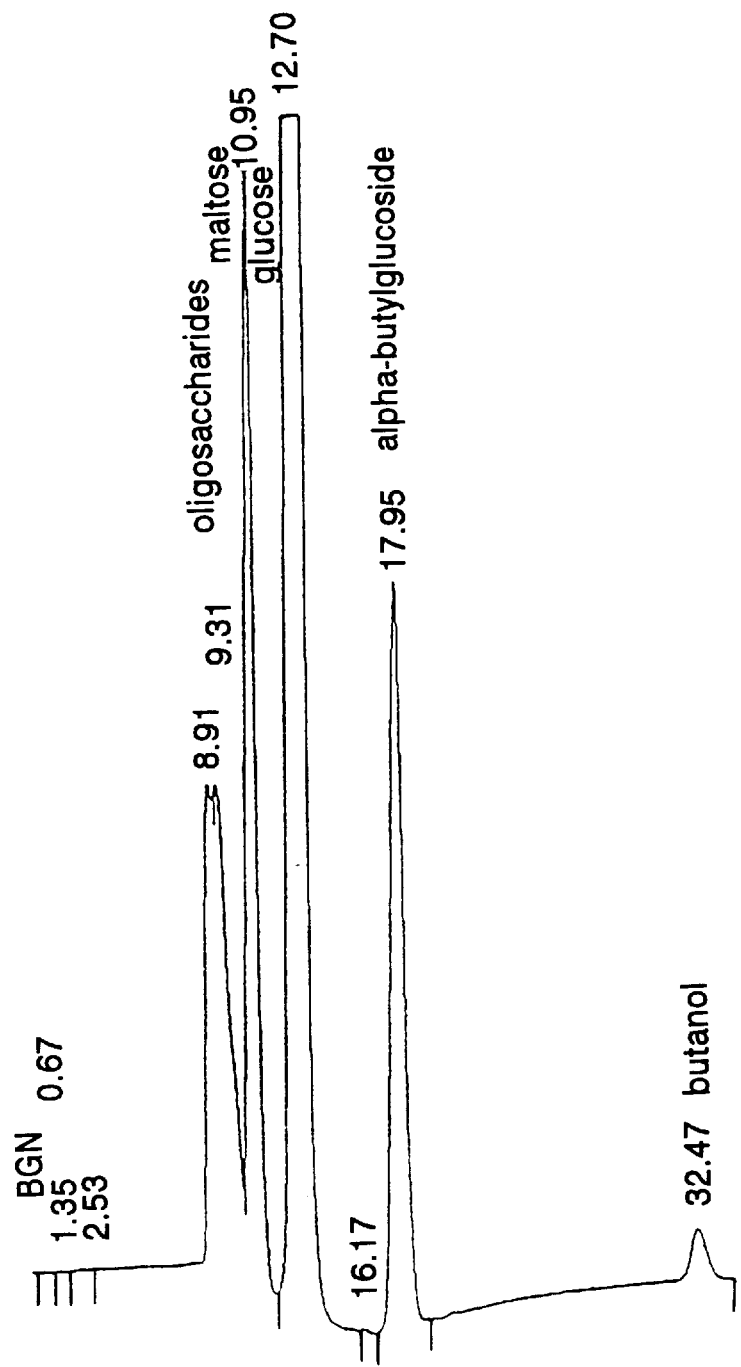
Figure 2C:
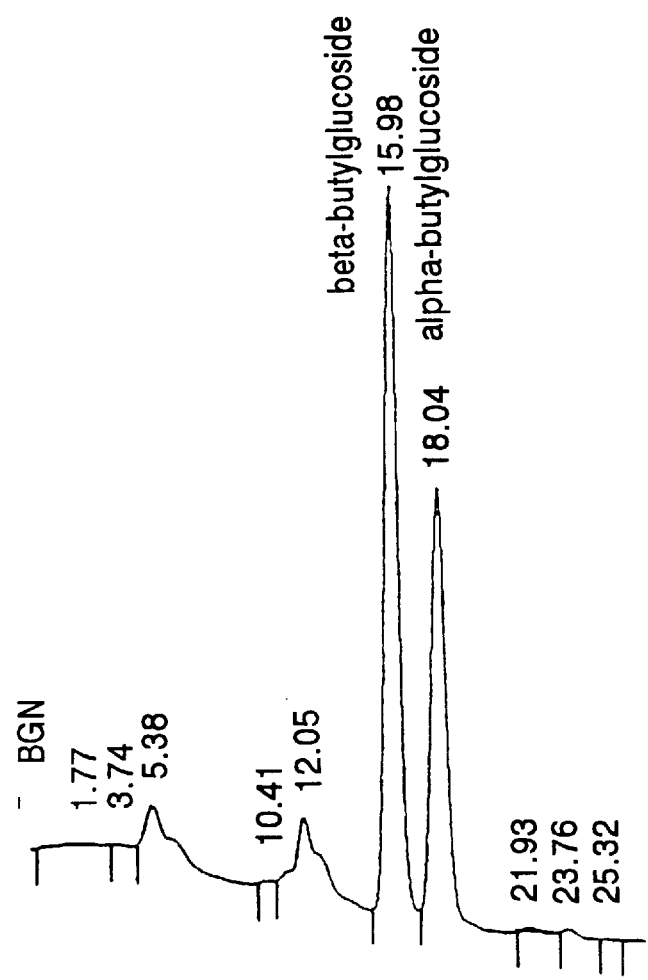

These media were analyzed as in Example 3. The chromatograms obtained are presented in FIGS. 2 and 3. The α-butylglucoside concentration is 12 g/l (51 mM) in the one-phase liquid medium and 7 g/L (30 mM) in the two-phase liquid medium.

The α-transglucosidase from *Aspergillus niger* is very effective for the synthesis of α-alkylglucoside.

Example 6

Production of α-butylglucoside palmitic esters by enzymatic esterification of α-butylglucoside A medium was prepared in the following way:

palmitic acid (PROLABO, France): 10.85 g

α-D-butylglucoside: 10 g

The α-D-butylglucoside was prepared according to the method of Example 1.

The mixture is brought to 75° C., the melting temperature of palmitic acid. After homogenization, 1 g of Lipozyme®, a lipase from *Mucor miehei,* immobilized on a solid support (NOVO INDUSTRI, Denmark) is added.

After incubation for 3 days, the reaction medium is diluted with 210 ml of diethyl ether (SDS, France), and subsequently filtered in order to remove the Lipozyme®. After filtration, 50 ml of sodium hydroxide (NaOH 0.02N) are added in order to dissolve the remaining palmitic acid in the aqueous phase, as well as the remaining α-butylglucoside, in the form of a sodium salt.

The organic phase (diethyl ether) containing the palmitic acid esters is evaporated under vacuum, in order to remove all trace of remaining solvent.

16.5 g of esters are finally obtained (mixture of monoesters and diesters of α-D-butylglucopyranoside: butyl 6-O-palmityl-α,D-glucopyranoside and butyl 2,6-di-O-palmityl-α,D-glucopyranoside). Characterization of the reaction products was done by T.L.C. and by proton and $^{13}$C N.M.R.

Example 7

Production of α-butylglucoside lauric esters by enzymatic esterification of α-butylglucoside A medium was prepared in the following way:

Lauric acid (MERCK, Germany): 8.5 g

α-D-butylglucoside: 10 g

The α-D-butylglucoside was prepared according to the method of Example 1.

The mixture is brought to 45° C., the melting temperature of lauric acid. After homogenization, 1 g of Lipozyme®, a lipase from *Mucor miehei,* immobilized on a solid support (NOVO INDUSTRI, Denmark) is added.

After incubation for 3 days, the reaction medium is diluted with 210 ml of diethyl ether (SDS, France), and subsequently filtered in order to remove the Lipozyme®. After filtration, 50 ml of sodium hydroxide (NaOH 0.02N) are added in order to dissolve the remaining lauric acid in the aqueous phase, as well as the remaining α-butylglucoside, in the form of a sodium salt.

The organic phase (diethyl ether) containing the lauric acid esters is evaporated under vacuum, in order to remove all trace of remaining solvent.

15 g of esters are finally obtained (mixture of monoesters and diesters of α-D-butylglucopyranoside: butyl 6-O-lauryl-α,D-glucopyranoside and butyl 2,6-di-O-lauryl-α,D-glucopyranoside). Characterization of the reaction products was done by T.L.C. and by proton and $^{13}$C N.M.R.

Example 8

Production of α-butylglucoside stearic esters

The method of Example 7 was repeated using:

Stearic acid: 1.2 g

α-D-butylglucoside: 1 g

The mixture is brought to 78° C. and 0.15 g of Lipozyme® is added.

The product was characterized by $^{13}$C-N.M.R. It was a mixture mainly consisting of butyl 6-O-stearyl-α,D-glucopyranoside (approximately 80%) and butyl 2,6-di-O-stearyl-α,D-glucopyranoside (approximately 20%).

We claim:

1. A process for the enzymatic manufacture of α-glucoside esters, which comprises the following steps 1) placing an acyclic alcohol, or a mixture of acyclic alcohols, having a solubility in water of at least 2.7% v/v at 20° C., in contact with starch, maltodextrins or maltose present in an initial concentration in the reaction of approximately 100 g/l to approximately 400 g/l in the presence of a first purified enzymatic preparation having α-transglucosylation activity, wherein said preparation is free of β-glucosidase activity so as to produce α-glucosides ; 2) contacting the α-glucosides so produced with at least one fatty acid and a second enzymatic preparation having lipase activity so as to produce α-glucoside esters, and 3) recovering the α-glucoside esters.

2. The process according to claim 1, wherein the first enzymatic preparation consists of an enzyme having α-transglucosylation activity or of several enzymes such that each has an α-transglucosylation property or such that their combined enzymatic activities confer α-transglucosylation activity on the enzymatic preparation.

3. The process according to claim 1 wherein the first enzymatic preparation comprises α-transglucosidases, originating from a fungus.

4. The process according to claim 3, wherein the fungus is *Talaromyces duponti, Aspergillus niger, Aspergillus oryzae* or *Aspergillus batatae.*

5. The process of claim 1, wherein the starch is a native starch and the first enzymatic preparation comprises a hydrolase.

6. The process according to claim 5 wherein the hydrolase is an endo-amylase.

7. The process according to claim 5 wherein the hydrolase is α-amylase.

8. The process according to claim 5, wherein the process of step 1) comprises simultaneous contacting of the starch with an endo-amylase and an α-transglucosidase.

9. The process according to claim 5 wherein the native starch is derived from cereals, from tubers, from leguminous plants, or from any other plant.

10. The process according to claim 9 wherein the cereal is wheat, corn, barley, oats, rice, rye, buckwheat, sorghum and triticale.

11. The process according to claim 9 wherein the tuber is potato or manioc.

12. The process according to claim 9 wherein the leguminous plant is peas or beans.

13. The process according to claim 9 wherein the cereals are in the form of whole grains or fractions of grains.

14. The process according to claim 13 wherein the grain fractions result from an enzymatic, chemical, thermal or mechanical treatment of the grain.

15. The process according to claim 13 wherein the mechanical treatment is grinding.

16. The process according to claim 1 wherein the starch is in the form of soluble starch.

17. The process according to claim 16 wherein the soluble starch results from an acidic or enzymatic prehydrolysis.

18. The process of claim 1, wherein the alcohol is a mono alcohol or a polyol.

19. The process of claim 18, wherein the alcohol is ethanol, n-propanol, isopropanol, n-butanol, isobutanol, tert-butanol, n-pentanol, isopentanol, hexanediol, or a mixture of at least two of these alcohols.

20. The process of claim 19, wherein the alcohol is mono alcohol containing from 2 to 5 carbon atoms, the product of the process being a α-alkylglucoside ester.

21. The process of claim 19, wherein the alcohol is a mono alcohol containing four carbon atoms and the product of the process is a α-butylglucoside ester.

22. The process of claim 1 wherein the contacting of the α-glucoside with the fatty acid(s) and the lipase in step 2) is carried out at a temperature at which the fatty acid(s) is a liquid and the reaction medium is free from solvent.

23. The process of claim 1 wherein the fatty acid contains from 8 to 20 carbon atoms.

24. The process of claim 23 wherein the fatty acid contains from 8 to 16 carbon atoms.

25. The process of claim 1, wherein the process of step 1) is carried out between 20° C. and 70° C., and at a pH between 3 and 7.

26. The process of claim 1, wherein the process of step 1) is carried out between 20° C. and 50° C.

27. The process of claim 1, wherein the process of step 1) is carried out at a pH between 4 and 6.

* * * * *